(12) United States Patent
Kang et al.

(10) Patent No.: US 7,794,708 B2
(45) Date of Patent: Sep. 14, 2010

(54) PHARMACEUTICAL COMPOSITION FOR PREVENTING AND TREATING RESTENOSIS COMPRISING PEROXIREDOXIN 2 PROTEIN AS AN ACTIVE INGREDIENT AND COMPOSITION FOR SCREENING THERAPEUTICS OF RESTENOSIS COMPRISING PEROXIREDOXIN 2 GENE OR ITS PROTEIN PRODUCT, AND METHOD FOR SCREENING THERAPEUTICS OF RESTINOSIS USING SAID COMPOSITION

(75) Inventors: Sang-Won Kang, Seoul (KR); Min-Hee Choi, Kyunggi-do (KR)

(73) Assignee: EWHA University-Industry Collaboration Foundation, Seoul (KR)

( * ) Notice: Subject to any disclaimer, the term of this patent is extended or adjusted under 35 U.S.C. 154(b) by 108 days.

(21) Appl. No.: 11/832,597

(22) Filed: Aug. 1, 2007

(65) Prior Publication Data
US 2007/0292406 A1 Dec. 20, 2007

Related U.S. Application Data

(63) Continuation of application No. PCT/KR2006/000289, filed on Jan. 25, 2006.

(30) Foreign Application Priority Data

Feb. 3, 2005 (KR) ...................... 10-2005-0009875

(51) Int. Cl.
*A61K 38/43* (2006.01)
*A61K 38/44* (2006.01)
(52) U.S. Cl. ..................................... 424/94.1; 424/94.4
(58) Field of Classification Search ........................ None
See application file for complete search history.

(56) References Cited
U.S. PATENT DOCUMENTS
2002/0168353 A1 11/2002 Lynn et al.

OTHER PUBLICATIONS

Choi et al. (Regulation of PDGF signaling and vascular remodeling by peroxiredoxin II, Nature, vol. 435, May 19, 2005, pp. 347-353).*
Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp: 8-9, 2002.*
Rabilloud T. et al., Biochem J. 312:699-705, 1995.
Lee TH et al., Blood, 101(12):pp. 5033-5038, 2003.
Ten Berge D et al "Prx1 and Prx2 are upstream regulators of sonic hedgehog and control cell proliferation during mandibular arch morphogenesis" In Development 2001 vol. 128, No. 15, pp. 2929-2938.
Jones FS et al. "Prx1 controls vascular smooth muscle cell proliferation and tenascin-C expression and is unregulated with Prx2 in pulmonary vascular disease" In Circ Res 2001, vol. 89, No. 2, pp. 131-138.
Kim H et al "Role of peroxiredoxins in regulating intracellular hydrogen peroxide and hydrogen peroxide-induced apoptosis in thyroid cells" In J. Biol Chem, 2000, vol. 275. No. 24, pp. 18266-18270.

* cited by examiner

*Primary Examiner*—Suzanne M. Noakes
*Assistant Examiner*—Jae W Lee
(74) *Attorney, Agent, or Firm*—Joseph Hyosuk Kim; JHK Law

(57) ABSTRACT

Disclosed herein is a pharmaceutical composition for the prophylaxis and treatment of restenosis, comprising a peroxiredoxin 2 (Prx II) protein as an active ingredient. Optionally, the composition may contain other active ingredients suppressive of restenosis at the carotid artery, the coronary artery, the peripheral artery, and the renal artery. Also, a composition and a method are provided for screening therapeutics for restenosis. This screening composition comprises a peroxiredoxin 2 gene or protein. Together with the method, the composition is useful for searching and developing therapeutics for restenosis.

6 Claims, 11 Drawing Sheets

PHARMACEUTICAL COMPOSITION FOR PREVENTING AND TREATING RESTENOSIS COMPRISING PEROXIREDOXIN 2 PROTEIN AS AN ACTIVE INGREDIENT AND COMPOSITION FOR SCREENING THERAPEUTICS OF RESTENOSIS COMPRISING PEROXIREDOXIN 2 GENE OR ITS PROTEIN PRODUCT, AND METHOD FOR SCREENING THERAPEUTICS OF RESTENOSIS USING SAID COMPOSITION

CROSS-REFERENCE TO RELATED APPLICATION

The present invention is a continuation application of PCT/KR2006/000289, filed Jan. 25, 2006, which claims benefit of priority to Korean patent application 10-2005-0009875, filed Feb. 3, 2005.

TECHNICAL FIELD

The present invention relates to a pharmaceutical composition for the prophylaxis and treatment of restenosis (renarrowing), a composition for screening therapeutics for restenosis, and a method for screening therapeutics for restenosis using the same.

BACKGROUND ART

Peroxiredoxin (Prx) is a scavenger of hydrogen peroxide and alkyl hydroperoxides in living organisms (Chae, H. Z. et al., Proc. Nat. Acad. Sci. 91: 7017-7021, 1994). There are six distinct mammalian Prx isozymes, types I to VI, that are detected in a wide range of tissues (Rhee, S G et al., IUBMB Life, 52:35~41, 2001). These have been found to have potent antioxidant activities in vivo. All of the known mammalian Prxs, except for type VI, utilize thioredoxin as an electron donor, and thus were formerly known as thioredoxin peroxidases.

In addition to their antioxidant activity, Prxs have been implicated in various cellular functions including cell proliferation and differentiation, enhancement of natural killer cell activity, protection of radical-sensitive proteins, heme metabolism, and intracellular signaling (Nemoto Y, et al., Gene, 91:261~265, 1990; Prosperi M T, et al., Genomics, 19:236~241,1994; Tsuji K, et al., Biochem J. 307:377~381, 1995; Shau H, et al., Immunogenetics, 40:129~134,1994; Watabe S, et al., Biochem Biophys Res Commun. 213:1010~1016, 1995; Iwahara S, et al., Biochemistry, 34:13398~13406, 1995; Wen S T, et al., Genes Dev. 11:2456~2467, 1997). The biochemical characteristics revealed from cultured animal cell studies show that Prx may be one of those that play important roles in maintaining cellular redox potential.

Of these antioxidant proteins, 2-cys peroxiredoxin type II (Prx II) is a cellular peroxidase that eliminates endogenous $H_2O_2$ produced in response to growth factors including platelet-derived growth factor (PDGF) and epidermal growth factor (EGF).

It is known that Prx II is located in abundance in the cytoplasm of cells, binds to integral membrane proteins or cell membranes via its C-terminal region, and has a high affinity for $H_2O_2$ (Km for $H_2O_2$ <10 μm).

Also, Prx II is found to be highly expressed in erythrocytes and to play a protective role against reactive oxygen species (ROS)-mediated damage in these cells, and is induced at the early stages of erythroid differentiation prior to hemoglobin accumulation (Rabilloud T, et al., Biochem J. 312:699-705, 1995).

Platelet-derived growth factor (PDGF) is a potent mitogenic and migratory factor that regulates the tyrosine phosphorylation of a variety of signaling proteins through the generation of endogenous $H_2O_2$. Particularly, PDGF stimulates the proliferation and migration of smooth muscle cells during vascular remodeling. In this regard, Prx II serves as an important regulator for the PDGF-mediated generation of $H_2O_2$, but its precise function in signal transduction has yet to be proven.

Based on the observation that Prx II-/- mice have hemolytic anemia, Lee T H et al., suggested that Prx II plays a major role in protecting RBCs from oxidative stress in mice (Lee T H et al., Blood, 101(12):pp 5033-5038, 2003). U.S. Pat. Publication No. 2002/0168353 discloses a composition for the treatment of HIV infection, comprising purified type I Peroxiredoxin and type II Peroxiredoxin.

Restenosis, or renarrowing, is said to recur in as many as 50% of stenosis cases or more, as determined by coronary angiography after coronary angioplasty. Being a major obstacle to the successful treatment of cardiovascular diseases, restenosis occurs in about 30% of patients who receive coronary angioplasty (balloon dilatation and stent insertion).

Restenosis, although the precise mechanism thereof. must be further revealed, is known to be attributed to the fact that growth factors and cytokines are locally secreted due to vascular endothelial cell injury during angioplasty or balloon dilatation and induce smooth muscle cell proliferation and migration through autocrine and paracrine mechanisms, leading to the narrowing of artery lumens. Hence, smooth muscle cell proliferation has recently been recognized as a clinical problem that is important in the effectiveness of coronary angioplasty (Bauters C, Isner J M, Prog Cardiovasc Dis. 40(2):107-116, 1997, U.S. Pat. Nos. 6,780,406 and 6,740, 678).

Extensive studies have been conducted to reduce or prevent restenosis. Particularly, many attempts have been made to regulate smooth muscle cell proliferation, using angiotensin converting enzyme (ACE) inhibitors, antisense RNAs for cell cycle regulatory proteins, and thymidine kinase genes (Rakugi et al, J. Clin. Invest., 93:339-346, 1994; Simons et al., Nature, 359:67-70, 1992; U.S. Pat. No. 6,780,406).

Leading to the present invention, the intensive and thorough study on intracellular functions of Prx II, conducted by the present inventors, resulted in the finding that Prx II is involved in vascular muscle cell migration, thereby being used in preventing or reducing vascular restenosis.

DISCLOSURE

Technical Solution

Accordingly, the present invention has been made keeping in mind the above problems occurring in the prior art, and an object of the present invention is to provide a pharmaceutical composition for the prophylaxis and treatment of vascular restenosis, comprising Prx II as an active ingredient.

Another object of the present invention is to provide a composition for screening therapeutics for restenosis.

A further object of the present invention is to provide a method for screening therapeutics for restenosis using the composition.

In accordance with an embodiment, the present invention pertains to a composition for the prophylaxis and treatment of vascular restenosis (renarrowing), comprising Prx II as an active ingredient.

Particularly, the composition comprising Prx II as an active ingredient in accordance with the present invention may be used for the prophylaxis and treatment of restenosis in the carotid artery, the coronary artery, the peripheral artery, and the renal artery.

In addition, the composition comprising Prx II as an active ingredient in accordance with the present invention is useful for preventing and treating restenosis attributable to hardening chronically occurring in grafted vessels or angioplasted segments or to short-term proliferation after angioplasty.

In addition to Prx II, the composition of the present invention may further contain other ingredients having inhibitory activity against restenosis.

Prx II has inhibitory activity against various cellular events including receptor tyrosine phosphorylation through growth factor signaling, vascular smooth muscle cell proliferation and migration, and neointimal thickening. This protein can be expressed by the base sequence of a prx II gene, listed in SEQ. ID. NO. 1, that encodes the amino acid sequence listed in SEQ. ID. NO. 2.

Prx II (gene loci Prdx2) is a cellular peroxidase that eliminates endogenous $H_2O_2$ produced in response to growth factors such as PDGF and EGF. The enzyme suppresses the amplification of intracellular signal transduction by inhibiting site-specific phosphorylation at PDGFRβ-PLCγ1. Through this mechanism, Prx II leads to the suppression of the proliferation, migration and neointimal thickening of vascular smooth muscle cells.

Upon stimulation with PDGF, the intracellular levels of $H_2O_2$ and phosphorylated proteins in Prx II-deficient embryonic fibrocytes increase. In Prx II-deficient cells stimulated with PDGF, PLCγ1 (phospholipase gamma 1) is phosphorylated particularly on tyrosine-783 and tyrosine-1253. Also, a phosphorylation increase is found only on tyrosine 579/581 and 857 out of the phosphorylation residues of PDGFRβ. However, the re-expression of wild-type Prx II within the cells returns these cellular events back to the suppression of tyrosine inhibition.

Prx II was also found to suppress the tyrosine phosphorylation of PDGFRβ in a site-specific manner, as well as cell migration in both human primary smooth muscle cells and mouse embryonic fibroblasts.

After being injured, the carotid artery of Prx II-deficient mice (Prx II−/− mice) undergoes more severe neointimal thickening during restenosis than does that of wild-type mice.

Taking advantage of the fact that during vascular remodeling, the loss of Prx II functions results in increasing the migration of smooth muscle cells, a pharmaceutical composition comprising Prx II, which suppresses the migration and neointimal thickening of smooth muscle cells, can be used as a medication for the diagnosis, prevention and treatment of cardiovascular diseases caused by smooth muscle cell migration, such as restenosis (Ferns G A, et al., Science. 1991 Sep. 6; 253(5024):1129-32; Heldin C H, Westermark B. Physiol Rev. 1999 October; 79(4):1283-316).

In the present invention, it is suggested that Prx II is an $H_2O_2$-based signal regulator that plays a special role in PDGFR signal transduction and can be a new target protein in the treatment of cardiovascular diseases.

In addition to the active ingredient Prx II, the composition of the present invention may contain pharmaceutically acceptable and physiologically suitable additives. Vehicles, disintegrants, sweeteners, binders, coatings, dilatants, lubricants, talc, and/or flavors may be used in the composition.

The composition of the present invention comprising Prx II as an active ingredient may be formulated in combination with at least one pharmaceutically acceptable carrier.

For liquid formulations, physiological saline, sterile saline, Ringer's solutions, buffered saline, albumin injections, dextrose solutions, maltodextrose solutions, glycerol, ethanol and combinations thereof may be used as vehicles. If necessary, other conventional additives such as antioxidants, buffers, bacteriostatics, and the like, may be added. Also, together with diluents, dispersants, surfactants, binders, lubricants and the like, the composition of the present invention may be formulated into pills, capsules, granules, and tablets as well as injection forms, such as solutions, suspensions, emulsions, etc. Further, the composition of the present invention may be formulated according to the methods described in Remington's Pharmaceutical Science, Mack Publishing Company, Easton Pa.

In accordance with the present invention, the composition comprising Prx II as an active ingredient may be administered in the form of granules, powders, coated tablets, capsules, suppositories, syrups, juices, suspensions, emulsions, injectable solutions, or sustained release agents.

As for the administration of the composition of the present invention comprising Prx II as an active ingredient, it may be achieved in a conventional manner through one of intravenous, intraarterial, intraabdominal, intramuscular, intrathoracic, transdermal, intranasal, inhalation, local, rectal, oral, intraocular, or subcutaneous routes, or the like.

Factors determining the dose of the composition comprising Prx II as an active ingredient include the type and severity of disease, the content and kind of the active and other ingredients, the dosage form of the composition, the age, body weight, physical condition, sex and diet of patients, the administration time interval, administration route, release rate of the composition, treatment time periods, co-administered drugs, etc. For adults, the composition may be administered once or many times a day in a total daily dose from 0.1 to 10 mg of Prx II per kg of body weight.

In accordance with another embodiment, the present invention pertains to a method for preventing and treating cardiovascular diseases caused by smooth muscle cell migration, such as vascular restenosis, by administering Prx II.

The present invention is intended to suppress the migration or neointimal thickening of smooth muscle cells after vessel injury in patients with cardiovascular diseases by administering Prx II thereto, thereby preventing vascular restenosis.

In the method for the prophylaxis and treatment of cardiovascular diseases caused by smooth muscle cell migration, such as restenosis, a Prx II protein may be administered via an intravenous, an intraarterial, an intraabdominal, an intramuscular, an intrathoracic, a transdermal, an intranasal, an inhalation, a local, a rectal, an oral, an intraocular, or a subcutaneous route.

In the method for the prophylaxis and treatment of cardiovascular diseases caused by smooth muscle cell migration, such as restenosis, Prx II is administered at a total daily dose from 0.01 mg to 100 mg per kg of body weight for adults one or many times a day, depending on various factors, including the type and severity of disease, the content and kind of the active and other ingredients, the dosage form of the composition, the age, body weight, physical condition, sex and diet of patients, the administration time interval, administration route, release rate of the composition, treatment time periods, co-administered drugs, etc.

In accordance with a further embodiment, the present invention pertains to the use of Prx II in the preparation of medical products for the prophylaxis and treatment of cardiovascular diseases caused by smooth muscle cell migration, such as restenosis.

In accordance with still a further embodiment, the present invention pertains to a composition for screening therapeutics for restenosis, comprising a mammalian Prx II gene.

The Prx II gene useful in the screening composition of the present invention may be selected from among the base sequence of SEQ. ID. NO. 1, base sequences of polymorphs of SEQ. ID. NO. 1, fragments of the base sequences, and combinations thereof.

In accordance with still another embodiment, the present invention pertains to a composition for screening therapeutics for restenosis, comprising a mammalian Prx II protein.

The Prx II protein useful in the screening composition of the present invention may be selected from among the amino acid sequence of SEQ. ID. NO. 2, proteins expressed from the base sequence of SEQ. ID. NO. 1, proteins expressed from the base sequences of polymorphs of SEQ. ID. NO. 1, Prx II polypeptide fragments having the same physiological activity as Prx II, and combinations thereof.

The screening composition of the present invention shows a relieving effect on restenosis.

In accordance with yet another embodiment, the present invention pertains to a method for screening therapeutics for restenosis using as a target material the screening composition comprising a Prx II gene.

In this method, the composition for screening therapeutics for restenosis comprising a Prx II gene is brought into contact with a test material to determine whether the test material enhances or suppresses the expression of the gene contained in the composition.

In accordance with yet a further embodiment, the present invention pertains to a method for screening therapeutics for restenosis using as a target material the screening composition comprising a Prx II protein.

In this method, the composition for screening therapeutics for restenosis comprising a Prx II protein is brought into contact with a test material to determine whether the test material enhances or suppresses the expression of the gene contained in the composition.

To screen therapeutics for restenosis with the composition comprising a Prx II gene, conventional methods useful for the analysis of reaction between DNA-DNA, DNA-RNA, DNA-protein, or DNA-compound may be used.

For example, available is a hybridization test for identifying the combination between the gene and a test material in vitro, a method for measuring the expression rate of the gene through Northern analysis after reaction between mammalian cells and a test material, quantitative PCR, and quantitative in-time PCR, or a reporter gene assay in which the gene coupled with a reporter gene is introduced into cells to react with a test material, followed by measuring the expression rate of the reporter protein.

In this regard, the composition of the present invention may contain distilled water or buffer for stabilizing the structure of nucleic acids, as well as the Prx II gene.

To screen therapeutics for restenosis with the composition comprising a Prx II protein, conventional methods useful for the analysis of reaction between proteins and proteins, or between proteins and compounds, may be used.

Available are, for example, screening methods utilizing the measurement of the activity of a test compound after reaction with the Prx II gene or protein, a yeast two-hybrid assay, a search for a phage-displayed peptide clone binding to a Prx II protein, HTS (high throughput screening) using a natural or chemical library, drug hit HTS, cell-based screening, or DNA array.

In this regard, the composition of the present invention may contain a buffer or reaction solution for safely maintaining the structure or activity of the protein in addition to the protein expressed from the Prx II gene. For in vivo assays, the composition of the present invention may further comprise a cell capable of expressing the protein or a cell containing a plasmid capable of expressing the protein in the presence of a promoter regulating the description of the gene.

In the screening method of the present invention, the test material may be a material that is assumed to have the possibility of being used as a therapeutic for restenosis according to conventional assays, or randomly selected nucleic acid sequences, proteins, extracts or natural materials.

If a test material is found to enhance the expression of the gene or the activity of the protein as measured by the screening method of the present invention, it can be a candidate therapeutic for restenosis. On the other hand, if a test material is found to suppress the expression of the gene or the activity of the protein as measured by the screening method of the present invention, its inhibitors can be also candidates for therapeutics for restenosis.

As such, the candidates for therapeutics for restenosis in accordance with the present invention may be leading compounds for the development of the therapeutics, which optimally modify the structure of the Prx II gene or protein so as to enhance the expression of the Prx II gene or the activity of the Prx protein.

Partially or fully enhancing the expression of mammalian Prx II genes or the activity of mammalian Prx II proteins, the materials thus obtained can be used to treat restenosis, coronary sclerosis, or other cardiovascular diseases caused due to the decreased expression of the Prx II gene or the decreased activity of the Prx II protein.

MODE FOR INVENTION

A better understanding of the present invention may be obtained through the following examples which are set forth to illustrate, but are not to be construed as the limit of the present invention.

EXAMPLE 1

Effect of Prx II on Tyrosine Phosphorylation of Endogenous Proteins 1-1) Observation of $H_2O_2$ Generation and Tyrosine Phosphorylation in Response to PDGF with Respective to Prx II Expression In this example, changes in endogenous $H_2O_2$ generation in response to PDGF were observed with respect to Prx II expression.

Wild-type Prx II(+/+) MEF (mouse embryonic fibroblasts) and Prx II(−/−) MEF were prepared according to a typical process well known in the art after Prx II(+/−) mice were mated with each other and embryos were excised from the mice on the 10th day of pregnancy (Kang, S. W. et al., J Biol Chem, 279, 2535-43 (2004)). PDGF-BB (25 ng/ml, Upstate) was used for PDGF stimulation.

The intracellular level of $H_2O_2$ was measured using 2,7-dichlorofluorescin diacetate (H2DCFDA, Molecular Probes Inc.).

When applied to cells, this compound crosses the plasma membrane and is transported into cells wherein it is hydrolyzed into impenetrable 2',7'-dichlorofluorescin (H2DCF) by endogenous esterases. This hydrolysate is oxidized by endogenous $H_2O_2$ to form 2',7'-dichlorofluoresceine (DCF) that has an excitation peak at 488 nm and an emission peak at 515 nm, enabling fluorescence detection.

Prx II(+/+) MEF and Prx II(−/−) MEFs were cultured in DMEM supplemented with 10% FBS (fetal bovine serum) in the presence of an antibiotic. Prior to PDGF stimulation, these cells were synchronized by serum starvation for 24 hours in DMEM supplemented with 0.5% FBS. PDGF stimulation was performed by treating the cells with PDGF at a density of 25 ng/ml for 5, 10, or 30 min. After completion of PDGF stimulation, the cells were washed with HBSS (HEPES-buffered saline solution) and allowed to react for an additional 5 min in 5 mM DCFH-DA. Fluorescence was measured using a confocal laser microscope (Kang, S. W. et al. J Biol Chem 273, 6297-302 (1998)).

Figure 1:
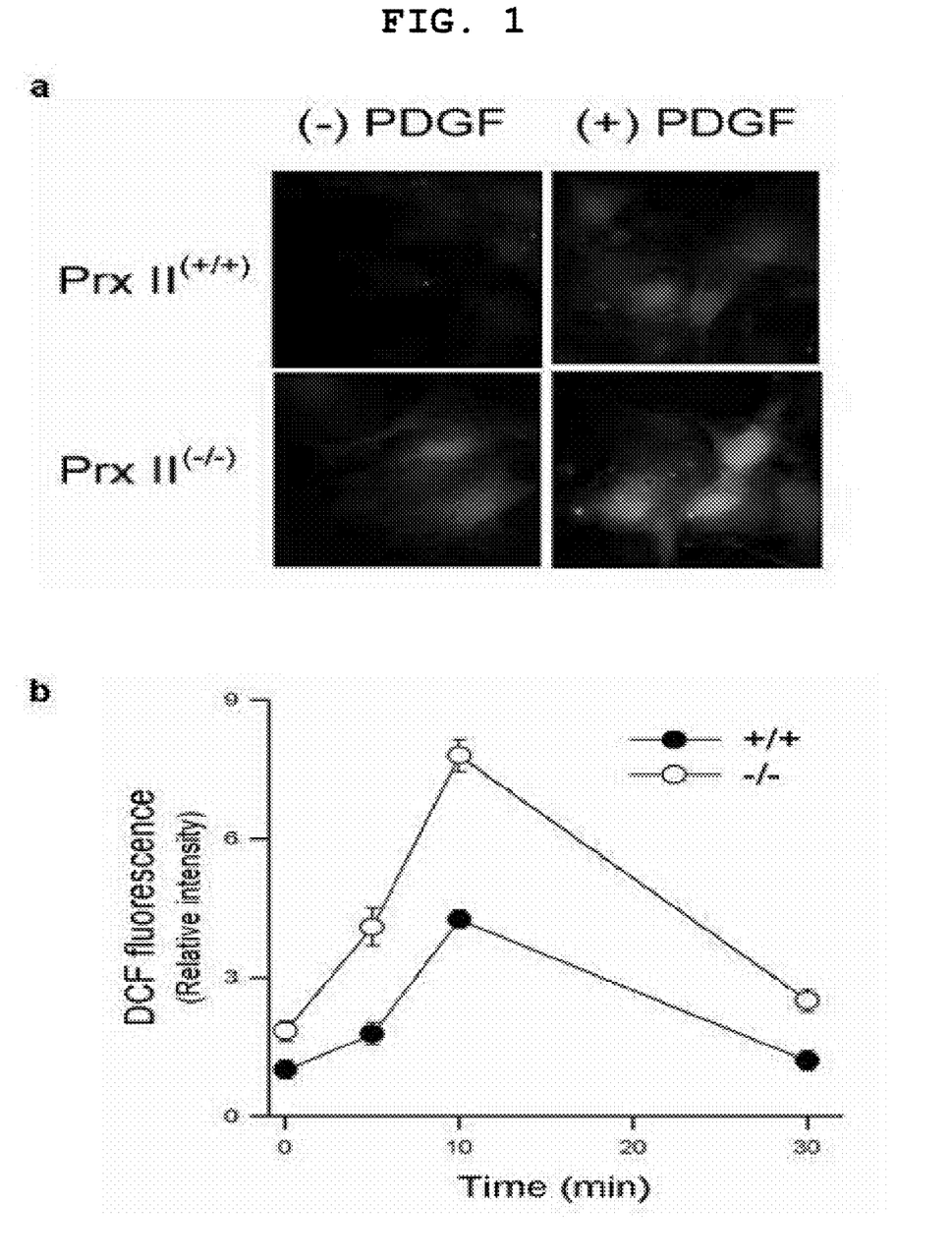
FIG. 1 shows intracellular $H_2O_2$ levels in normal MEF and Prx II(−/−) MEF in response to PDGF stimulation.

In FIG. 1a, there are photographs of 2',7'-DCF fluorescence taken 10 min after the PDGF-BB stimulation, showing that Prx II(−/−) MEFs are higher in endogenous $H_2O_2$ level than Prx II(+/+) MEFs both before and after PDGF stimulation.

In FIG. 1b, relative intensities of DCF are plotted against time, showing that the generation of $H_2O_2$ in the Prx II-deficient mouse cells was about twice as large as that in wild-type cells in response to PDGF and that the generation of $H_2O_2$ was temporally increased and returned to the base line within 30 min.

1-2) Observation of Tyrosine Phosphorylation of Endogenous Proteins

Following the treatment of Prx II(+/+) MEF and Prx II(−/−) MEF with PDGF as in Example 1-1, the phosphorylation of intracellular proteins over time was observed.

Proteins extracted from each cell were immunoblotted with an anti-phosphorylation antibody (4G10, Upstate) so as to analyze them for tyrosine phosphorylation. An anti-Prx II antibody (Labfrontier Co., Korea), and an anti-tubulin antibody (Sigma-Aldrich Co.) was used for immunoblotting and the results are given in FIG. 2.

Figure 2:
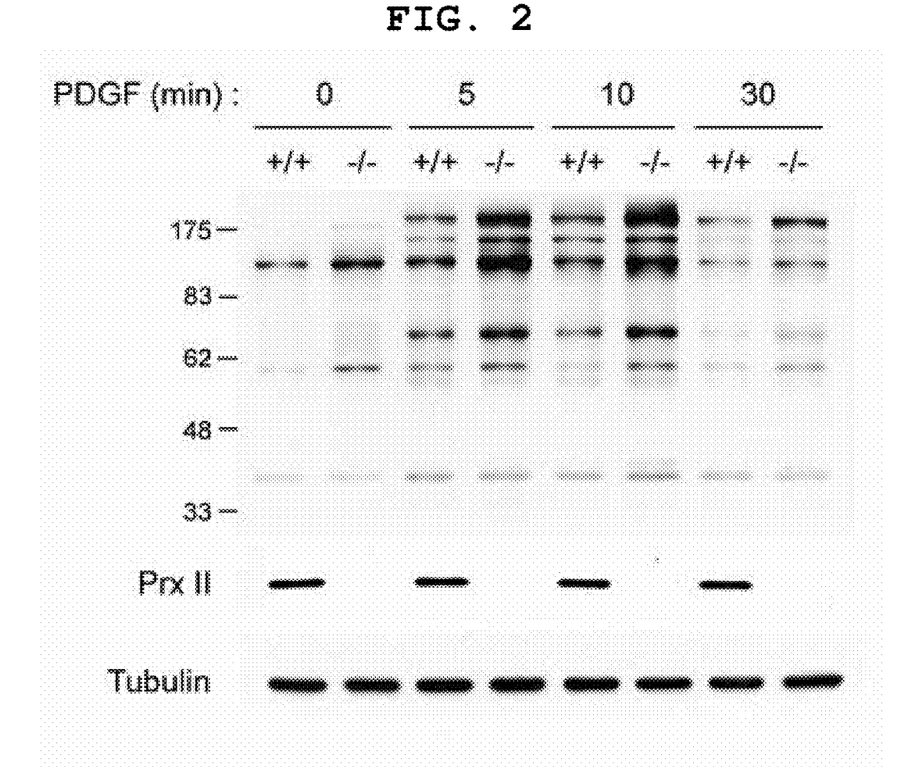
FIG. 2 shows levels of phosphorylation on total proteins in normal MEF and Prx II(−/−) MEF in response to PDGF stimulation.

Coincident with Example 1-1 with respect to $H_2O_2$ generation over time, the PDGF-induced tyrosine phosphorylation on proteins in the Prx II(−/−) MEFs was observed to dramatically increase compared to that in the wild-type MEFs (FIG. 2).

1-3) Observation of the phosphorylation of phospholipase C gamma 1 Using phospho-specific antibodies, Prx II expression was analyzed for the activation of downstream signaling molecules.

After treatment with PDGF, Prx II(+/+) MEFs and Prx II(−/−) MEFs were immunoblotted to determine phosphorylation on Src, PLCγ1, ERK2, and Akt proteins with time. In this regard, phospho-Src antibodies (Biosource), phospho-Akt antibodies (Cell Signaling Technology), and phospho-ERK antibodies (Cell Signaling Technology) were used and c-Src, Akt, PDGFRβ (M-20), and ERK2 were purchased from Santa Cruz Biotechnology. Anti-phospho-PLCγ1 (pY783 and pY1253) antibodies were prepared according to well-known methods (Sekiya F, et al., J Biol. Chem. 2004 279(31):32181-90).

Figure 3:
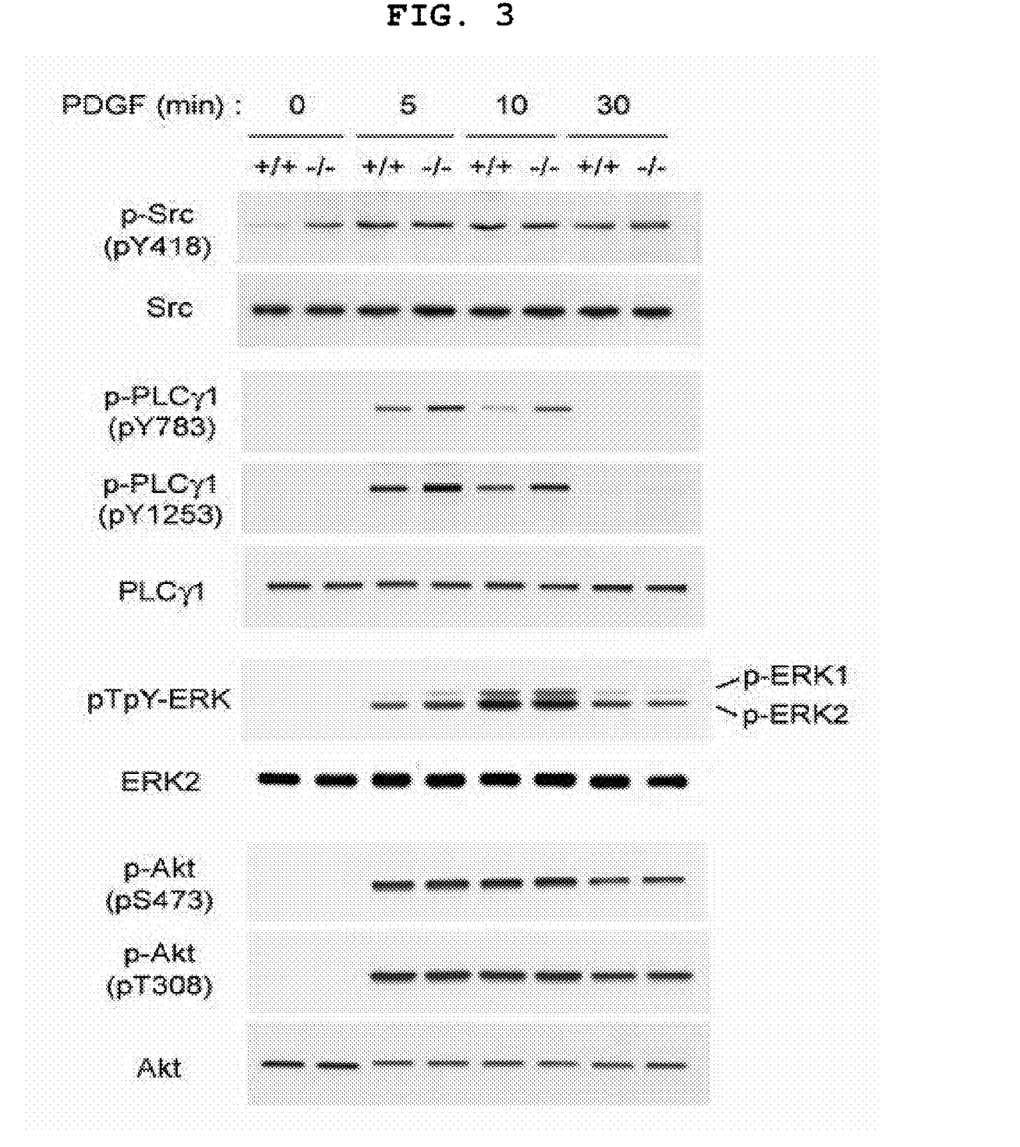
FIG. 3 shows levels of phosphorylation on individual signaling proteins in normal MEF and Prx II(−/−) MEF in response to PDGF stimulation.

As seen in FIG. 3, the residues Tyr783 and Tyr1253, known to be responsible for the activity of PLCγ1, were phosphorylated at higher rates in Prx II(−/−) MEFs than in the wild-type cells, but there were no changes in c-Src, ERK and Akt activation-dependent phosphorylation.

1-4) Regulation of Prx II in Site-Specific Phosphorylation for PDGFR Activation 1-4-1) Antibody Preparation Phosphor-specific antibodies against peptide regions corresponding to the seven well-known tyrosine residues of PDGFR (providing binding sites for signaling molecules having SH2 domains, such as c-Src, p85 subunit of PI-3K, GAP, Grb2, SHP-2, and PLCg, respectively) were prepared.

Phospho-peptide antigens (SynPep, USA) used for the production of phospho-specific PDGFR antibodies were as follows: pY579, DGHEpYIYVDPMQ; pY716, SAELpYSNALPVG; pY740, SDGGpYMDMSKDE; pY751, ESVDpYVPMLDMK; pY771, ESSNpYMAPYDNY; pY857, RDSNpYISKGSTF; pY1009, SSVLpYTAVQPNE; pY1021, GDNDpYIIPLPDP; (the phosphorylated tyrosine residue in each human PDGFR amino acid sequence was italicized).

The phospho-peptides were conjugated with keyhole limpet hemocyanin via glutaraldehyde and injected into rabbits. Rabbit anti-serum was purified using sequential affinity chromatography in columns filled with non-phosphorylated and phosphorylated peptide-conjugated Affigel-15 (Bio-Rad) agarose resins.

1-4-2) Regulation of Prx II in Site-Specific Phosphorylation for PDGFRβ Activation After being treated with PDGF, Prx II(+/+) MEF and Prx II(−/−) MEF cells were analyzed for PDGFRβ phosphorylation over time through an immunoblotting assay. Using anti-phospho –PDGFRβ antibodies, site-specific regulation was observed on the tyrosine residues.

Figure 4:
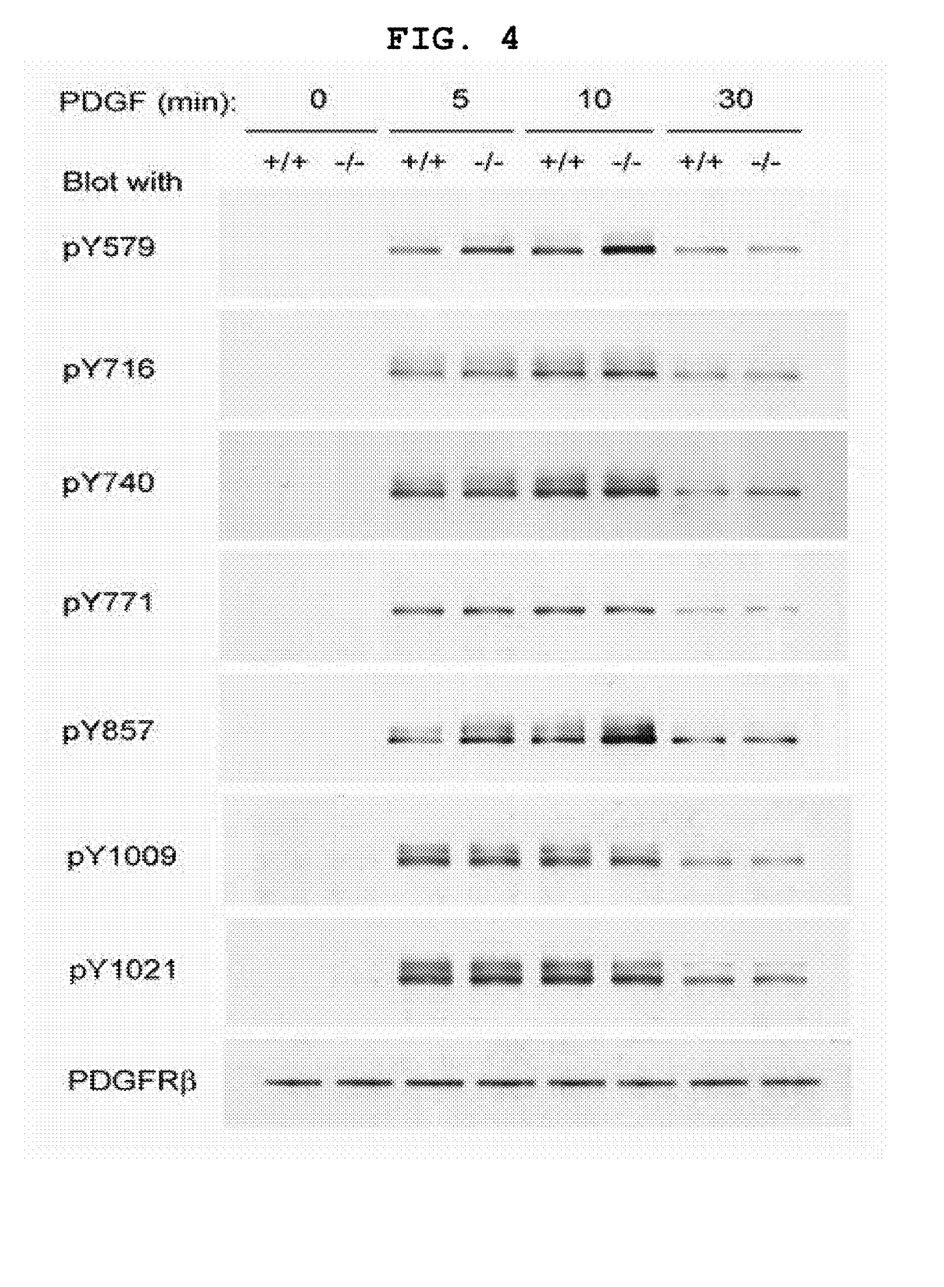
FIG. 4 shows levels of phosphorylation on various tyrosine residues of PDGFRβ in normal MEF and Prx II(−/−) MEF in response to PDGF stimulation.

As seen in FIG. 4, a significant increase in phosphorylation was observed only on Tyr 579/581 and Tyr 857 in Prx II(−/−) MEFs as compared with wild-type cells.

When Prx II is deficient, as described above, endogenous $H_2O_2$ is not eliminated so that downstream signaling molecules are activated. In this regard, site-specific phosphorylation was observed on the residues Y783 and Y1253 of PLCγ1 and the residues Y579/581 and Y857 of PDGFR. Also, the peroxidase activity of Prx II is essential for the site-specific regulation of PDGFR phosphorylation.

EXAMPLE 2

Observation of Cell Migration in Prx II-Reexpressed Prx II(−/−) MEF

An add-back rescue experiment, in which retrovirus was used to re-express human Prx II-wt in Prx II(−/−) MEFs, was performed to examine the influence of the re-expression on protein phosphorylation and migration.

2-1) Re-expression of Human Prx II-wt in Prx II(−/−) MEFs and Observation of Protein Phosphorylation Prx II(−/−) MEF was infected with retrovirus carrying a control gene or a human Prx II wild-type gene in order to examine the phosphorylation of cellular proteins.

Control retrovirus (C) and human Prx II-encoding retrovirus (P) were obtained from a stably transformed PT67 cell line and a transiently transformed Phoenix-ampho packing cell line (www.stanford.edu/group/nolan/index.html)

In advance of serum starvation, Prx II(−/−) MEFs were infected with human Prx II-encoding retrovirus (P) at 10 M.O.I. (multiplicity of infection) for two days to express Prx II therein.

Proteins were extracted from the prepared cells and analyzed for total phosphorylation and tyrosine phosphorylation on PLCγ1 and PDGFRβ through immunoblotting assay.

Figure 5:
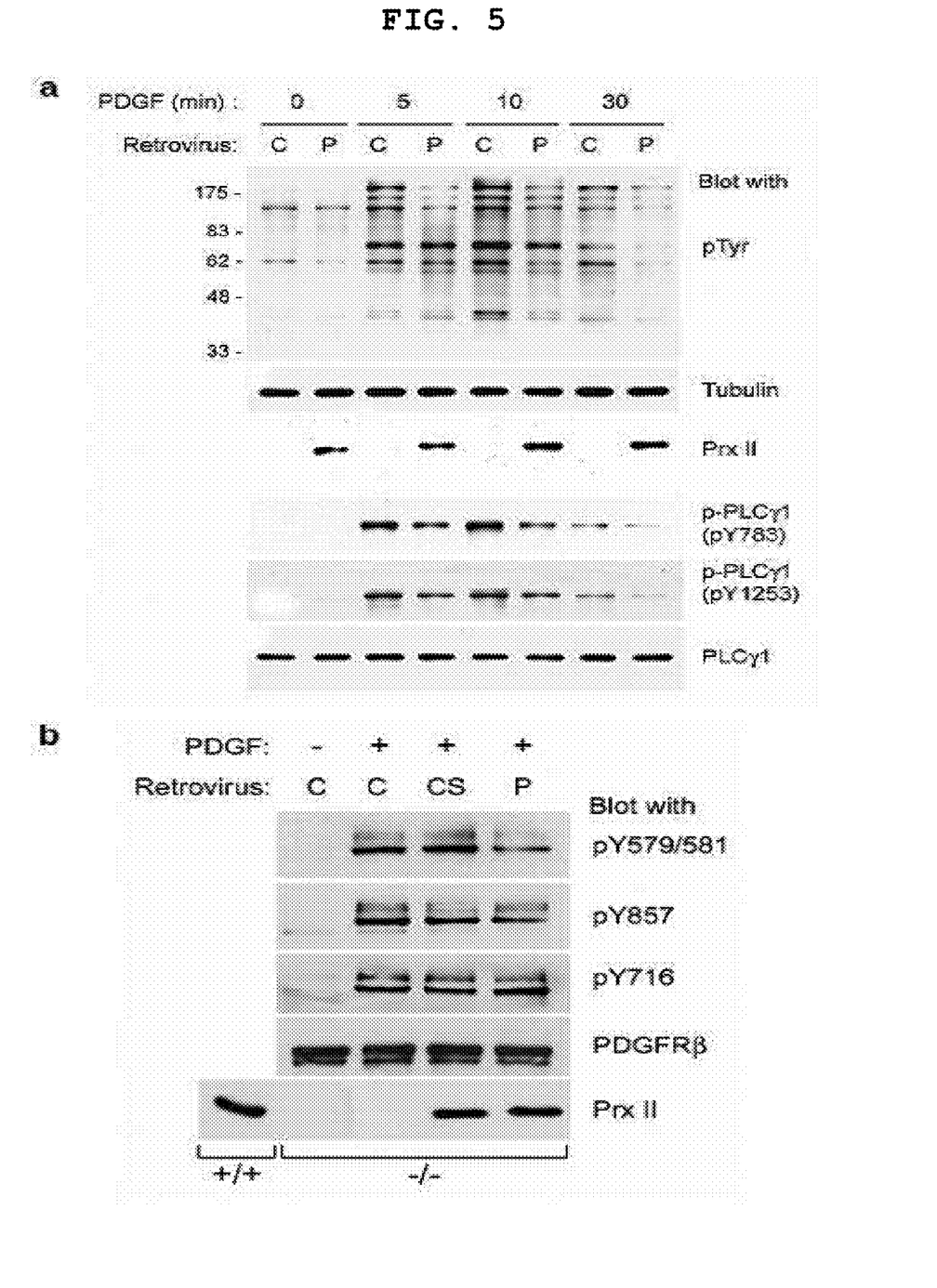
FIG. 5 shows levels of phosphorylation on total proteins and PLCγ1 when a human Prx II wild-type protein is expressed in mouse Prx II(−/−) MEF (a) and levels of phosphorylation on PDGFRβ in response to PDGF when human Prx II wild-type and inactivated mutant proteins were expressed in mouse Prx II(−/−) MEF (b).

In response to PDGF, as is apparent from the data of FIG. 5a, the Prx II-reexpressed cell was phosphorylated to a lesser extent than was the control cell, not only with respect to total proteins but also with respect to the Y783 and Y1253 of PLCγ1.

Also, as seen in FIG. 5b, the level of the reexpressed Prx II(−/−) MEF was similar to the wild-type MEF (Prx II(+/+)) with respect not only to intracellular Prx II level, but also to tyrosine phosphorylation of PDGFRβ in response to PDGF. Also, Prx II-reexpressed cells were found to have the Y579/581 and Y857 of PDGFR phosphorylated to a lesser extent.

Therefore, the re-expression of Prx II leads to the suppression of the tyrosine phosphorylation on PLC gamma and PDGFRβ.

2-2) Test for Migration of Mouse Embryonic Fibroblast (MEF)

The Prx II(−/−) MEF, in which Prx II was reexpressed in the same manner as above, was examined for cell migration.

An assay for MEF cell migration was performed in a 24-well Transwell culture chamber (Costar; 8-μm pore size). The membrane of the Transwell culture chamber was coated with gelatin B (1 μg/μl) and placed on a 24-well plate. In the lower compartment of the culture chamber, PDGF-BB (25 ng/ml) and DMEM, containing 0.1% bovine serum albumin were filled.

In the upper compartment of the chamber, MEFs ($5 \times 10^4$) were incubated at 37° C./5% $CO_2$ for 6 hours. The cells that moved toward the lower part of the filter were stained with 0.6% hematoxylin and 0.5% eosin and counted under an optical microscope. Cell counts were performed in four fields of view selected at random through two independent experiments and were expressed as means ±S.D.

Figure 6:
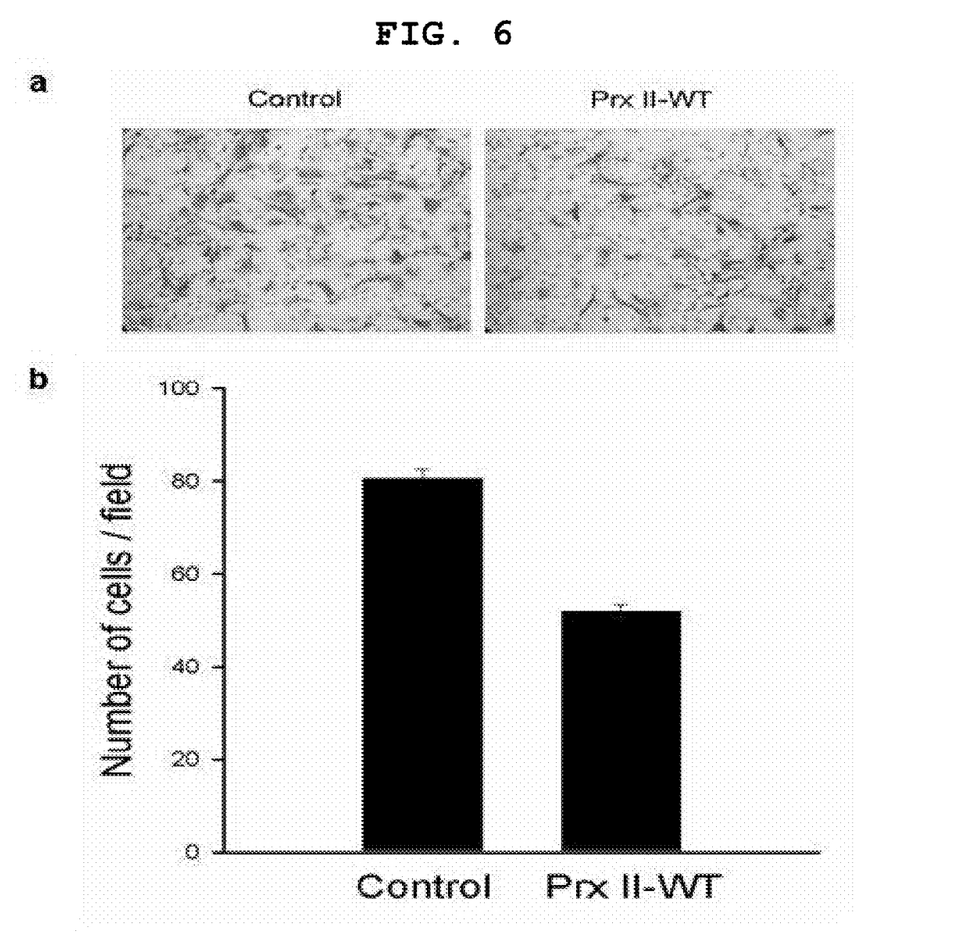
FIG. 6 shows cell migration towards PDGF (a) and the number of cells that migrated (b) when a human Prx II wild-type protein is expressed in mouse Prx II(−/−) MEF.

As understood from data of FIG. 6, lower counts resulted for the wt Prx II-reexpressed cells than for the control, implying that Prx II suppressed PDGF-induced fibroblast proliferation and migration.

EXAMPLE 3

Effect of Prx II on Vascular Smooth Muscle Cell Migration

PDGF is an important factor for smooth muscle cell proliferation and migration during vascular remodeling. The selective regulation of Prx II in the PDGFRβ-PLCγ1 pathway of human and murine vascular smooth muscle cells (VSMCs) was observed in vitro.

3-1) Prx II Expression and Cellular Protein Phosphorylation in Human VSMCs

Human aortic smooth muscle cells were cultured according to the instructions of the manufacturer (Clonetics Co., USA).

The cells were sub-cultured four times and immunoblotted with an antibody against α-smooth muscle actin (Sigma). Prior to PDGF-BB (25 ng/ml, Upstate) stimulation, the primary cells were subjected to serum starvation (0.5% FBS) for 24 hours.

Control retrovirus (C) and human Prx II-encoding retrovirus (P) were obtained from a stably transformed PT67 cell line and a transiently transformed Phoenix-ampho packing cell line (www.stanford.edu/group/nolan/index.html)

In advance of serum starvation, VSMCs were infected with human Prx II-encoding retrovirus (P) at 10 M.O.I. (multiplicity of infection) for two days.

Figure 7:
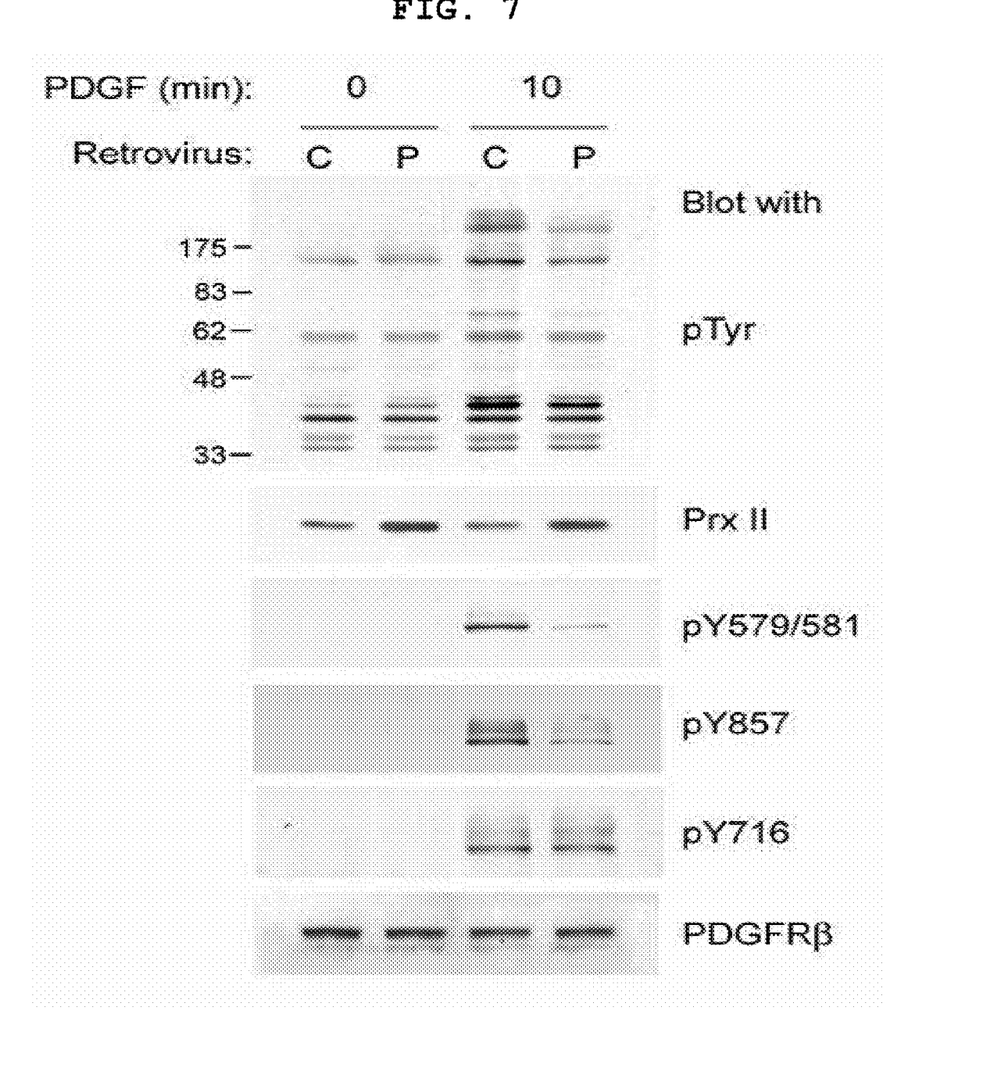
FIG. 7 shows levels of phosphorylation on total proteins and tyrosine residues of PDGFRβ in response to PDGF upon the overexpression of a Prx II wild-type protein in human VSMCs in which Prx II wild-type protein is expressed.

As understood from data of FIG. 7, neither the control (C) nor the human Prx II-encoding retrovirus-treated group (P) was phosphorylated on tyrosine residues 579/581, 857, and 716 of PDGFRβ before PDGF stimulation. 10 min after PDGF stimulation, phosphorylation on the Y579/581, and Y857 residues of PDGFRβ occurred to a significantly lesser extent in the human Prx II-encoding retrovirus-treated group (P) than in the control (C).

The overexpression of wild-type Prx II in human aortic VSMCs about three times as high as the endogenous expression of Prx II resulted in a significant decrease in phosphorylation on PLCγ1 and the Y579/581 and Y857 of PDGFR.

3-2) Test for Human VSMC Migration

In the human aortic smooth muscle cells prepared in Example 3-1), Prx II was examined for cell migration.

An assay for the human aortic smooth muscle cell migration was performed in a 24-well Transwell culture chamber (Costar; 8-μm pore size). The membrane of the Transwell culture chamber was coated with gelatin B (1 μg/μl) and placed on a 24-well plate. In the lower compartment of the culture chamber, PDGF-BB (25 ng/ml) and DMEM, containing 0.1% bovine serum albumin, were charged.

In the upper compartment of the chamber, VSMCs (5×104) were incubated at 37° C./5% $CO_2$ for 6 hours. The cells that moved toward the lower part of the filter were stained with 0.6% hematoxylin and 0.5% eosin and counted under an optical microscope. Cell counts were performed in four fields of view selected at random through two independent experiments and were expressed as means ±S.D.

Figure 8:
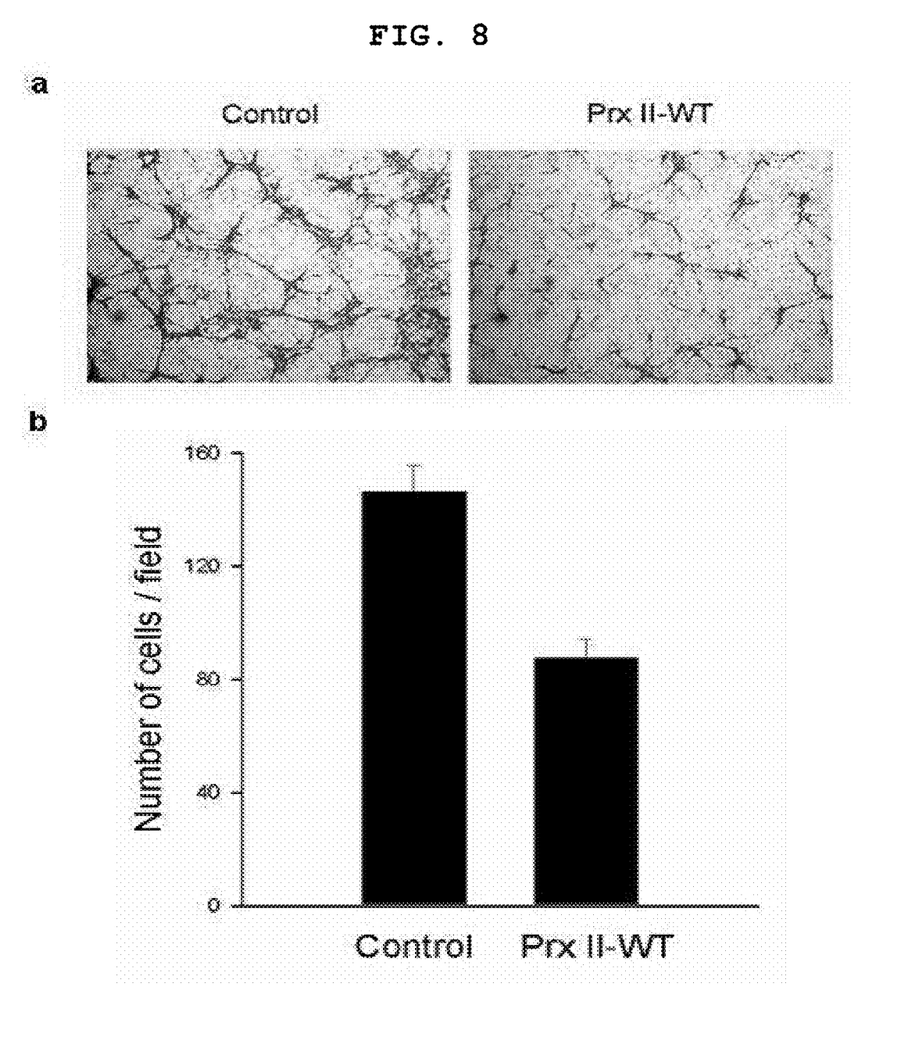
FIG. 8 shows cell migration towards PDGF (a) and the number of cells that migrated (b) when a Prx II protein is overexpressed in human VSMCs.

As can be understood from data of FIG. 8, lower counts resulted for the wt Prx II-reexpressed cells than for the control, implying that Prx II suppressed PDGF-induced smooth muscle cell migration.

3-3) Observation of Phosphorylation in Murine VSMCs

From wild-type mice and Prx II-deficient mice, both 10 weeks old, aortic smooth muscle cells were prepared according to a method described in the reference (Ohmi, K. et al., Biochem Biophys Res Commun, 238, 154-8 (1997)).

Proteins were extracted from each cell treated with PDGF and analyzed for the tyrosine phosphorylation of PDGFRβ by immunoblotting.

Figure 9:
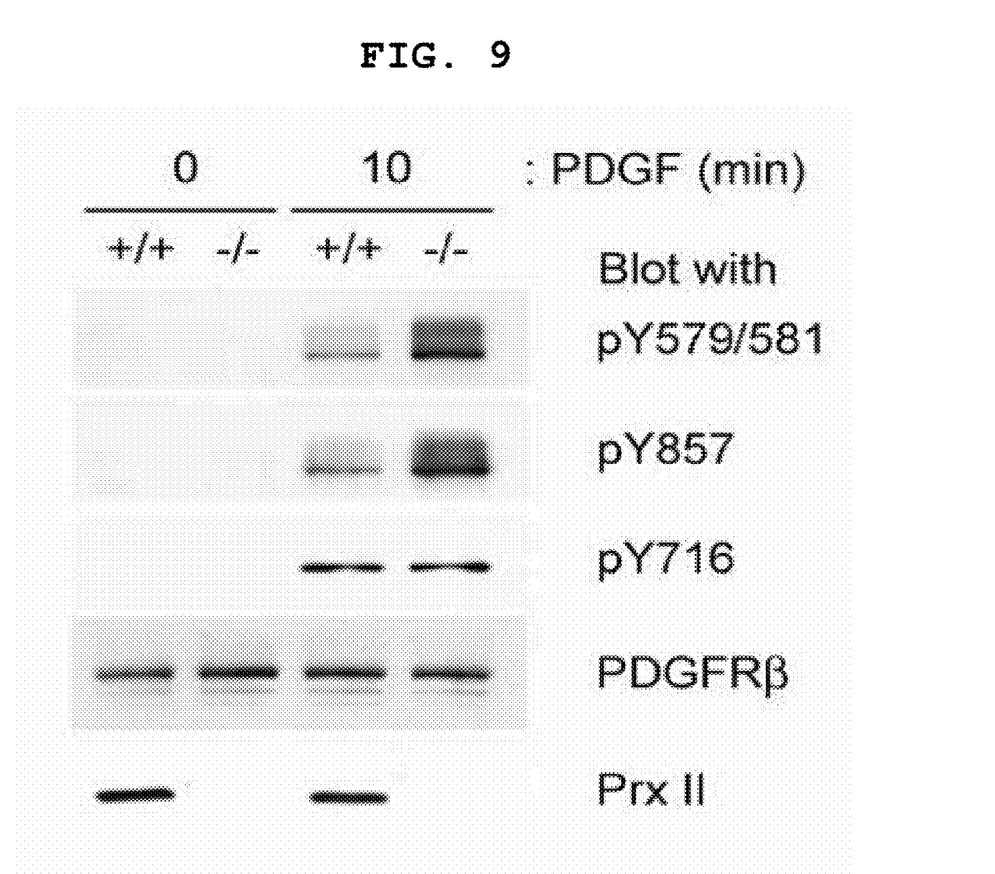
FIG. 9 shows the tyrosine phosphorylation of PDGFRβ when VSMCs isolated from Prx II(−/−) mice are treated with PDGF.

When treated with PDGF, as seen in FIG. 9, VSMCs prepared from the artery of Prx II(−/−) mice showed more intensive site-specific phosphorylation of PDGFRβ than did those prepared from the artery of wild-type mice.

3-4) Effect of Prx II on Restenosis of Mouse Carotid Artery after Vessel Injury

After wild-type and Prx II(−/−) mouse carotid arteries were injured, the effect of Prx II on the neointimal thickening of VSMCs during restenosis was observed in vivo.

Transluminal wire injuries to mouse left common carotid arteries were performed as specified in the literature (Schober, A. et al., Circulation, 109, 380-5 (2004)).

10-week-old male mice were anesthetized, followed by exposing the left external carotid artery and coagulating its branches using electric currents. A 0.016-inch flexible angioplasty guide wire was advanced 1 cm through the transverse arteriotomy of the external carotid artery, and endothelial denudation was achieved by 6 passes along the common carotid artery. After one week, the common carotid artery was excised after transcardiac perfusion-fixation with 3.7% formaldehyde and heparinized saline and then paraffin-embedded.

5 consecutive tissue slices (taken at 100 μm intervals and each 3 μm thick) were obtained from the middle region of the common carotid artery. For morphological observation, each slice was stained with hematoxylin and eosin. Cross-sectional areas of the medial and neointimal layers were analyzed with a computerized analysis system and program (MetaMorpho imaging v5.0, Molecular Devices) with the aid of a digital camera system (CoolSNAP camera system with BX51 microscopy, Olympus).

Figure 10:
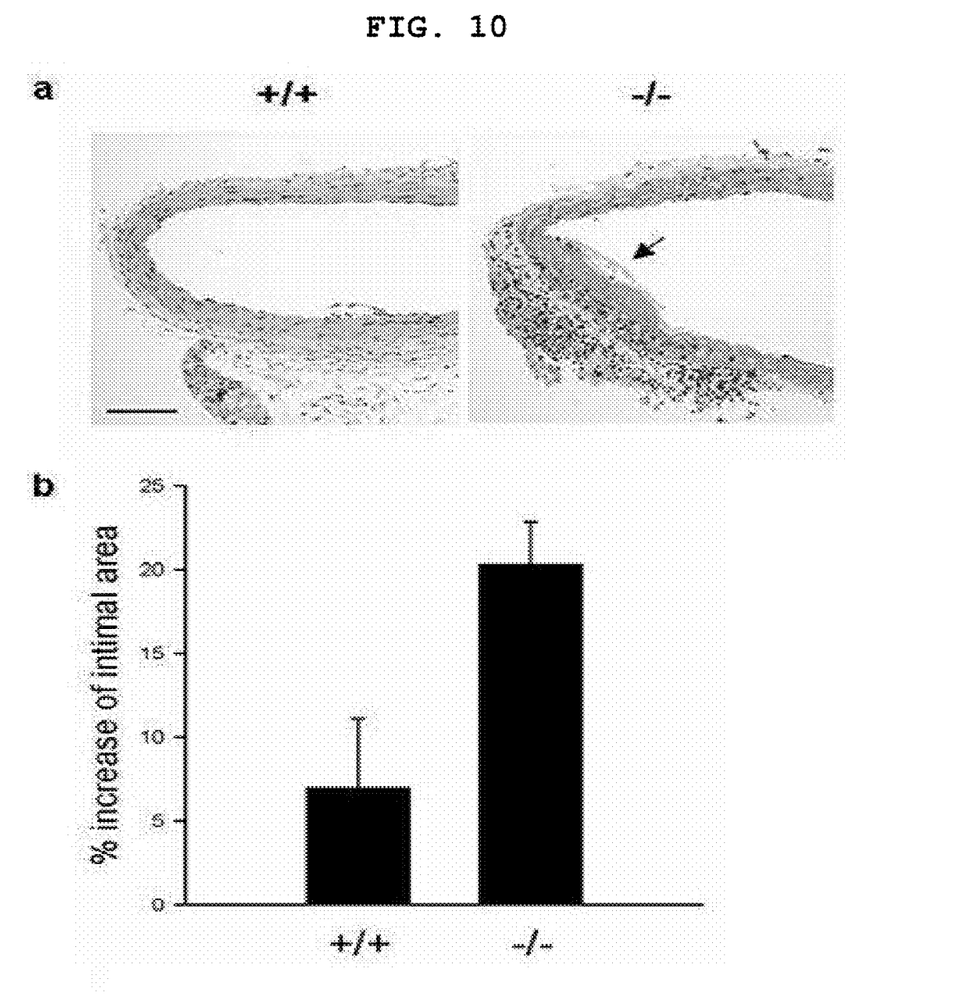
FIG. 10 shows neointimal thickening after vessel injury in normal and Prx II(−/−) mice.

Neither the wild-type mice nor the Prx II(−/−) mice underwent the neointimal thickening of the carotid artery that was not injured. When injured with the wire, the carotid artery of the Prx II(−/−) mice had neointimal layers significantly thicker than those of the wild-type mice, as shown in FIG. 10*a*. VSMCs were accumulated on the neointimal layer, as indicated by the arrow in FIG. 10*a*.

The bar graph of FIG. 10*b* was drawn on the basis of percentage increase of neointimal plaque area relative to medial area (mean ±S.E.M., n=5, P<0.01). As seen in the graph, the % increase of neointimal area of Prx II(−/−) mice increased to about three times that of wild-type mice.

Therefore, the loss of Prx II function leads to the promotion of VSMC migration during vascular remodeling.

EXAMPLE 4

Plasma PDGF Neutralization

In order to prevent the neointimal thickening caused by PDGF-induced signal transduction activation, a test for plasma PDGF neutralization was performed.

control IgG or an anti-PDGF antibody (Cat. No. AF-220-NA, R&D systems) was injected into Prx II(−/−) three times a day over one week starting one day before injuring the carotid artery. At a dose of 5 μg per 20 g of body weight per injection, the antibody was injected intravenously on −1 and 0 day and then subcutaneously until +4 day. Afterwards, the left external carotid artery was observed for change in neointimal thickness and the results were expressed as percentages of neointimal plaque thickness relative to the medial layer (mean ±S.E.M., n=4, P<0.01).

Figure 11:
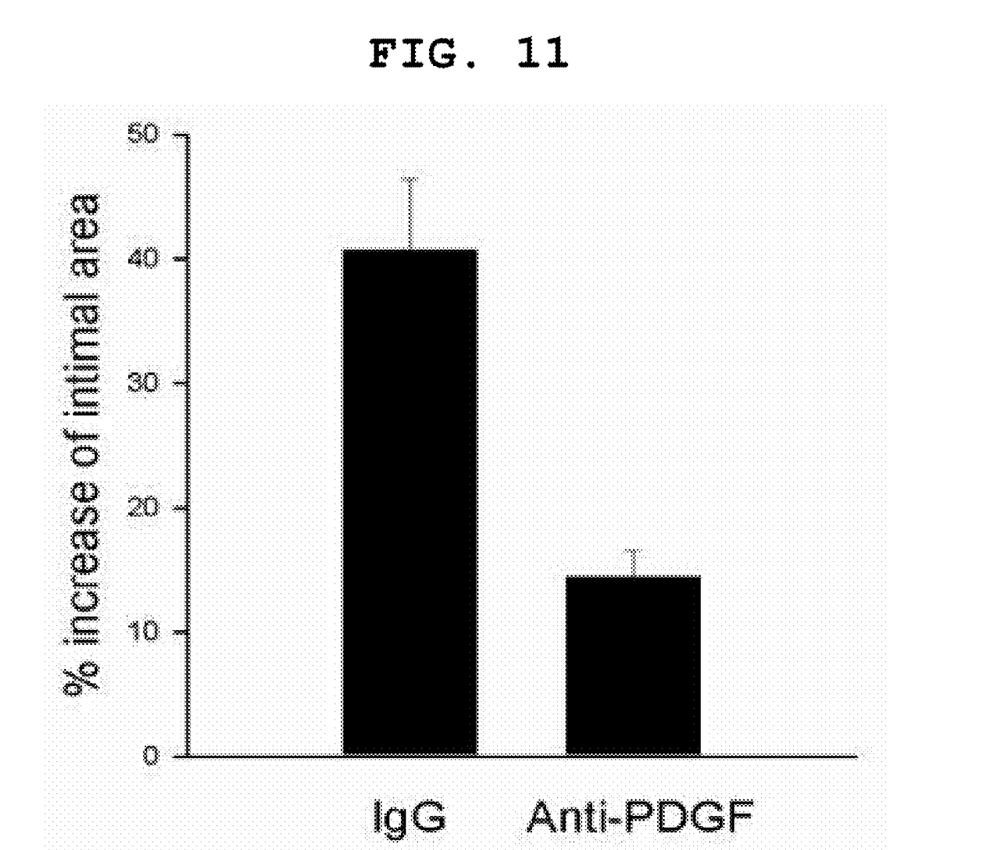
FIG. 11 shows neoinitmal thickening after vessel injury in Prx II(−/−) mice injected with control IgG and an anti-PDGF antibody.

As is understood from data of FIG. 11, anti-PDGF antibody administration significantly reduces the neointimal thickening.

Prx II suppresses PDGF-induced smooth muscle cell migration while the loss of Prx II functions results in improving smooth muscle cell migration during vascular remodeling. Thus, the pharmaceutical composition of the present invention can be useful for the prophylaxis and treatment of restenosis.

Also, the composition comprising a Prx II gene or protein in accordance with the present invention can be used for screening materials, that can react therewith, as candidates for developing therapeutics for restenosis.

INDUSTRIAL APPLICABILITY

As described above, the present invention provides a pharmaceutical composition, comprising Prx II as an active ingredient, for the prophylaxis and treatment of restenosis, based on the research finding that the function of Prx II is highly responsible for the migration of smooth muscle cells during vascular remodeling.

Further, the screening composition and method according to the present invention is very useful in searching for and developing therapeutics for restenosis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for the treatment of restenosis in a subject, comprising administering to said subject a pharmaceutical composition comprising human peroxiredoxin 2 (Prx II) having the amino acid sequence of SEQ ID NO:2 as an active ingredient.

2. The method of claim 1, wherein the restenosis occurs in a carotid artery, a coronary artery, a peripheral artery, and/or a renal artery.

3. The method of claim 1, wherein the restenosis is caused due to the chronic hardening process performed in grafted vessels or angioplasted segments or to short-term cell proliferation after angioplasty.

4. The method of claim 1, wherein said pharmaceutical composition is administered in an amount sufficient to inhibit smooth muscle cell migration.

5. A method for treating restenosis in a subject, comprising administering to said subject a pharmaceutical composition comprising human peroxiredoxin 2 (Prx II) as an active ingredient to inhibit smooth muscle cell migration.

6. The method according to claim 5, wherein the Prx II has the amino acid sequence of SEQ ID NO:2.

* * * * *

SEQUENCE LISTING

<160> NUMBER OF SEQ ID NOS: 2

<210> SEQ ID NO 1
<211> LENGTH: 1039
<212> TYPE: DNA

```
<213> ORGANISM: Homo sapiens
<220> FEATURE:
<221> NAME/KEY: 5'UTR
<222> LOCATION: (1)..(150)
<220> FEATURE:
<221> NAME/KEY: gene
<222> LOCATION: (1)..(1039)
<223> OTHER INFORMATION: Peroxiredoxin 2 (PRDX2)
<220> FEATURE:
<221> NAME/KEY: CDS
<222> LOCATION: (151)..(744)
<220> FEATURE:
<221> NAME/KEY: terminator
<222> LOCATION: (745)..(747)
<220> FEATURE:
<221> NAME/KEY: 3'UTR
<222> LOCATION: (748)..(1039)
<220> FEATURE:
<221> NAME/KEY: polyA_signal
<222> LOCATION: (984)..(989)
<220> FEATURE:
<221> NAME/KEY: polyA_site
<222> LOCATION: (1008)..(1008)

<400> SEQUENCE: 1
```

| | |
|---|---|
| gctcgtccgc tccctccccc gcgccgtgca cgtcttggtt cgggccgggc ataaaaggct | 60 |
| tcgcggccca gggctcactt ggcgctgaga acgcgggtcc acgcgtgtga tcgtccgtgc | 120 |
| gtctagcctt tgcccacgca gctttcagtc atg gcc tcc ggt aac gcg cgc atc<br>                                         Met Ala Ser Gly Asn Ala Arg Ile<br>                                           1                5 | 174 |
| gga aag cca gcc cct gac ttc aag gcc aca gcg gtg gtt gat ggc gcc<br>Gly Lys Pro Ala Pro Asp Phe Lys Ala Thr Ala Val Val Asp Gly Ala<br>  10                   15                   20 | 222 |
| ttc aaa gag gtg aag ctg tcg gac tac aaa ggg aag tac gtg gtc ctc<br>Phe Lys Glu Val Lys Leu Ser Asp Tyr Lys Gly Lys Tyr Val Val Leu<br>25                   30                   35                 40 | 270 |
| ttt ttc tac cct ctg gac ttc act ttt gtg tgc ccc acc gag atc atc<br>Phe Phe Tyr Pro Leu Asp Phe Thr Phe Val Cys Pro Thr Glu Ile Ile<br>                 45                   50                 55 | 318 |
| gcg ttc agc aac cgt gca gag gac ttc cgc aag ctg ggc tgt gaa gtg<br>Ala Phe Ser Asn Arg Ala Glu Asp Phe Arg Lys Leu Gly Cys Glu Val<br>              60                   65                   70 | 366 |
| ctg ggc gtc tcg gtg gac tct cag ttc acc cac ctg gct tgg atc aac<br>Leu Gly Val Ser Val Asp Ser Gln Phe Thr His Leu Ala Trp Ile Asn<br>        75                   80                   85 | 414 |
| acc ccc cgg aaa gag gga ggc ttg ggc ccc ctg aac atc ccc ctg ctt<br>Thr Pro Arg Lys Glu Gly Gly Leu Gly Pro Leu Asn Ile Pro Leu Leu<br>  90                   95                       100 | 462 |
| gct gac gtg acc aga cgc ttg tct gag gat tac ggc gtg ctg aaa aca<br>Ala Asp Val Thr Arg Arg Leu Ser Glu Asp Tyr Gly Val Leu Lys Thr<br>105                 110                 115               120 | 510 |
| gat gag ggc att gcc tac agg ggc ctc ttt atc atc gat ggc aag ggt<br>Asp Glu Gly Ile Ala Tyr Arg Gly Leu Phe Ile Ile Asp Gly Lys Gly<br>                 125                 130               135 | 558 |
| gtc ctt cgc cag atc act gtt aat gat ttg cct gtg gga cgc tcc gtg<br>Val Leu Arg Gln Ile Thr Val Asn Asp Leu Pro Val Gly Arg Ser Val<br>            140                 145               150 | 606 |
| gat gag gct ctg cgg ctg gtc cag gcc ttc cag tac aca gac gag cat<br>Asp Glu Ala Leu Arg Leu Val Gln Ala Phe Gln Tyr Thr Asp Glu His<br>  155                 160                 165 | 654 |
| ggg gaa gtt tgt ccc gct ggc tgg aag cct ggc agt gac acg att aag<br>Gly Glu Val Cys Pro Ala Gly Trp Lys Pro Gly Ser Asp Thr Ile Lys<br>170                 175                 180 | 702 |
| ccc aac gtg gat gac agc aag gaa tat ttc tcc aaa cac aat<br>Pro Asn Val Asp Asp Ser Lys Glu Tyr Phe Ser Lys His Asn | 744 |

-continued

```
Pro Asn Val Asp Asp Ser Lys Glu Tyr Phe Ser Lys His Asn
185                 190                 195 taggctggct aacggatagt gagcttgtgc ccctgcctag gtgcctgtgc tgggtgtcca      804
cctgtgcccc cacctgggtg ccctatgctg acccaggaaa ggccagacct gcccctccaa      864
actccacagt atgggaccct ggagggctag gccaaggcct tctcatgcct ccacctagaa      924
gctgaatagt gacgccctcc cccaagccca cccagccgca cacaggccta gaggtaacca      984
ataaagtatt agggaaaggt gtgaaaaaaa aaaaaaaaaa aaaaaaaaaa aaaaa          1039

<210> SEQ ID NO 2
<211> LENGTH: 198
<212> TYPE: PRT
<213> ORGANISM: Homo sapiens

<400> SEQUENCE: 2

Met Ala Ser Gly Asn Ala Arg Ile Gly Lys Pro Ala Pro Asp Phe Lys
1               5                   10                  15

Ala Thr Ala Val Val Asp Gly Ala Phe Lys Glu Val Lys Leu Ser Asp
                20                  25                  30

Tyr Lys Gly Lys Tyr Val Val Leu Phe Phe Tyr Pro Leu Asp Phe Thr
            35                  40                  45

Phe Val Cys Pro Thr Glu Ile Ile Ala Phe Ser Asn Arg Ala Glu Asp
        50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Arg Arg Leu Ser
            100                 105                 110

Glu Asp Tyr Gly Val Leu Lys Thr Asp Glu Gly Ile Ala Tyr Arg Gly
        115                 120                 125

Leu Phe Ile Ile Asp Gly Lys Gly Val Leu Arg Gln Ile Thr Val Asn
130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195
```